US011904082B2

United States Patent
Yonezawa et al.

(10) Patent No.: US 11,904,082 B2
(45) Date of Patent: Feb. 20, 2024

(54) ADSORBENT FOR CALCIPROTEIN PARTICLES, ADSORPTION REMOVAL SYSTEM, AND METHOD FOR UTILIZATION THEREOF

(71) Applicants: KANEKA CORPORATION, Osaka (JP); JICHI MEDICAL UNIVERSITY, Tokyo (JP)

(72) Inventors: Ai Yonezawa, Settsu (JP); Kana Watanabe, Settsu (JP); Makoto Kuroo, Shimotsuke (JP)

(73) Assignees: KANEKA CORPORATION, Osaka (JP); BROAD BEAN SCIENCE CO., LTD., Shimotsuke (JP)

( * ) Notice: Subject to any disclaimer, the term of this patent is extended or adjusted under 35 U.S.C. 154(b) by 667 days.

(21) Appl. No.: 16/322,686

(22) PCT Filed: Jul. 31, 2017

(86) PCT No.: PCT/JP2017/027717
§ 371 (c)(1),
(2) Date: Feb. 1, 2019

(87) PCT Pub. No.: WO2018/025809
PCT Pub. Date: Feb. 8, 2018

(65) Prior Publication Data
US 2020/0238253 A1 Jul. 30, 2020

(30) Foreign Application Priority Data
Aug. 1, 2016 (JP) .................... 2016-151390

(51) Int. Cl.
*B01D 15/00* (2006.01)
*C07K 1/14* (2006.01)
(Continued)

(52) U.S. Cl.
CPC ........ *A61M 1/3496* (2013.01); *A61M 1/3687* (2013.01); *B01D 15/00* (2013.01);
(Continued)

(58) Field of Classification Search
None
See application file for complete search history.

(56) References Cited

U.S. PATENT DOCUMENTS

| | | |
|---|---|---|
| 4,770,774 A | 9/1988 | Ida et al. |
| 4,830,847 A | 5/1989 | Benedict et al. |

(Continued)

FOREIGN PATENT DOCUMENTS

| | | |
|---|---|---|
| EP | 0 207 557 A2 | 1/1987 |
| EP | 0 236 509 A1 | 9/1987 |

(Continued)

OTHER PUBLICATIONS

Cai et al., "Fetuin-A-containing calciprotein particle levels can be reduced by dialysis, sodium thiosulphate and plasma exchange, Potential therapeutic implications for calciphylaxis?", Nephrology, vol. 18, No. 11, Nov. 1, 2013, pp. 724-727.
(Continued)

*Primary Examiner* — Kara M Peo
(74) *Attorney, Agent, or Firm* — Birch, Stewart, Kolasch & Birch, LLP

(57) ABSTRACT

The purpose of the present invention is to adsorb calciprotein particles. An adsorbent for calciprotein particles of the present invention is characterized in that the surface of a water-insoluble carrier is covalently bonded, through a hydrocarbon group, to at least one selected from the group consisting of amino group, carboxyl group, phosphate group, phosphono group, phosphino group, and thiol group.

18 Claims, 1 Drawing Sheet

(51) Int. Cl.
    *A61M 1/34*    (2006.01)
    *A61M 1/36*    (2006.01)
    *B01J 20/24*   (2006.01)
    *B01J 20/32*   (2006.01)

(52) U.S. Cl.
    CPC .......... *B01J 20/24* (2013.01); *B01J 20/3212* (2013.01); *B01J 20/3219* (2013.01); *B01J 20/3265* (2013.01); *B01J 20/3293* (2013.01); *C07K 1/14* (2013.01)

(56) References Cited

U.S. PATENT DOCUMENTS

| | | | |
|---|---|---|---|
| 5,821,193 | A | 10/1998 | Tani et al. |
| 6,719,998 | B1 | 4/2004 | Golomb et al. |
| 7,138,462 | B2 | 11/2006 | Smith et al. |
| 2002/0169294 | A1 | 11/2002 | Mizokami et al. |
| 2002/0187184 | A1 | 12/2002 | Golomb et al. |
| 2003/0013686 | A1 | 1/2003 | Golomb et al. |
| 2003/0027211 | A1 | 2/2003 | Price |
| 2004/0050784 | A1 | 3/2004 | Belew et al. |
| 2004/0102598 | A1 | 5/2004 | Alferiev et al. |
| 2004/0226874 | A1 | 11/2004 | Nanko et al. |
| 2004/0228829 | A1 | 11/2004 | Roberts et al. |
| 2004/0256324 | A1 | 12/2004 | Belew et al. |
| 2005/0059805 | A1 | 3/2005 | Mizokami et al. |
| 2005/0281809 | A1 | 12/2005 | Roberts et al. |
| 2007/0166385 | A1 | 7/2007 | Golomb et al. |
| 2007/0181499 | A1 | 8/2007 | Roberts et al. |
| 2010/0072860 | A1 | 3/2010 | Kim et al. |
| 2012/0063954 | A1 | 3/2012 | Passlick-Deetjen et al. |

FOREIGN PATENT DOCUMENTS

| | | |
|---|---|---|
| JP | 7-275697 A | 10/1995 |
| JP | 2002-520345 A | 7/2002 |
| JP | 2003-524025 A | 8/2003 |
| JP | 2004-508920 A | 3/2004 |
| JP | 2008-503273 A | 2/2008 |
| JP | 2012-533582 A | 12/2012 |
| JP | 2014-135976 A | 7/2014 |
| WO | WO 01/49295 A1 | 7/2001 |
| WO | WO 02/08249 A1 | 1/2002 |
| WO | WO2008/148174 A1 | 12/2008 |

OTHER PUBLICATIONS

European Search Report dated Feb. 7, 2020 for EP Application No. 17836914.6.

Novotna et al., "Immobilized metal affinity chromatography of phosphorylated proteins using high performance sorbents", Chromatographia, vol. 68, No. 5-6, Jul. 23, 2008, pp. 381-386.

Rayment et al., "Attenuation of protease activity in chronic wound fluid with bisphosphonate-functionalised hydrogels", Biomaterials, Elsevier Science Publishers BV, Barking, GB, vol. 29, No. 12, Jan. 31, 2008, pp. 1785-1795.

Yamabe et al., "Metal ion selectivity of macroreticular chelating cation exchange resins with phosphonic acid groups attached to phenyl groups of a styrene-divinylbenzene copolymer matrix", vol. 36, No. 15, Nov. 30, 2001, pp. 3511-3528.

Yavorskyy et al., "Detection of calcium phosphate crystals in the joint fluid of patients with osteoarthritis-analytical approaches and challenges", Analyst, vol. 133, No. 3, Jan. 1, 2008, pp. 302-318.

Hamano et al., "Fetuin-Mineral Complex Reflects Extraosseous Calcification Stress in CKD," J Am Soc Nephrol 21, 2010, pp. 1998-2007.

International Search Report (PCT/ISA/210) issued in PCT/JP2017/027717, dated Oct. 10, 2017.

Kuro-O. "Why is phosphate overload harmful?" Clinical Calcium vol. 24, No. 12, Nov. 28, 2014, pp. 41-48.

Smith et al., "Phosphorylated fetuin-A-containing calciprotein particles are associated with aortic stiffness and a procalcific milieu in patients with pre-dialysis CKD," Nephrol Dial Transplant 27, 2012, pp. 1957-1966.

European Communication pursuant to Article 94(3) EPC for European Application No. 17836914.6, dated Jan. 18, 2023.

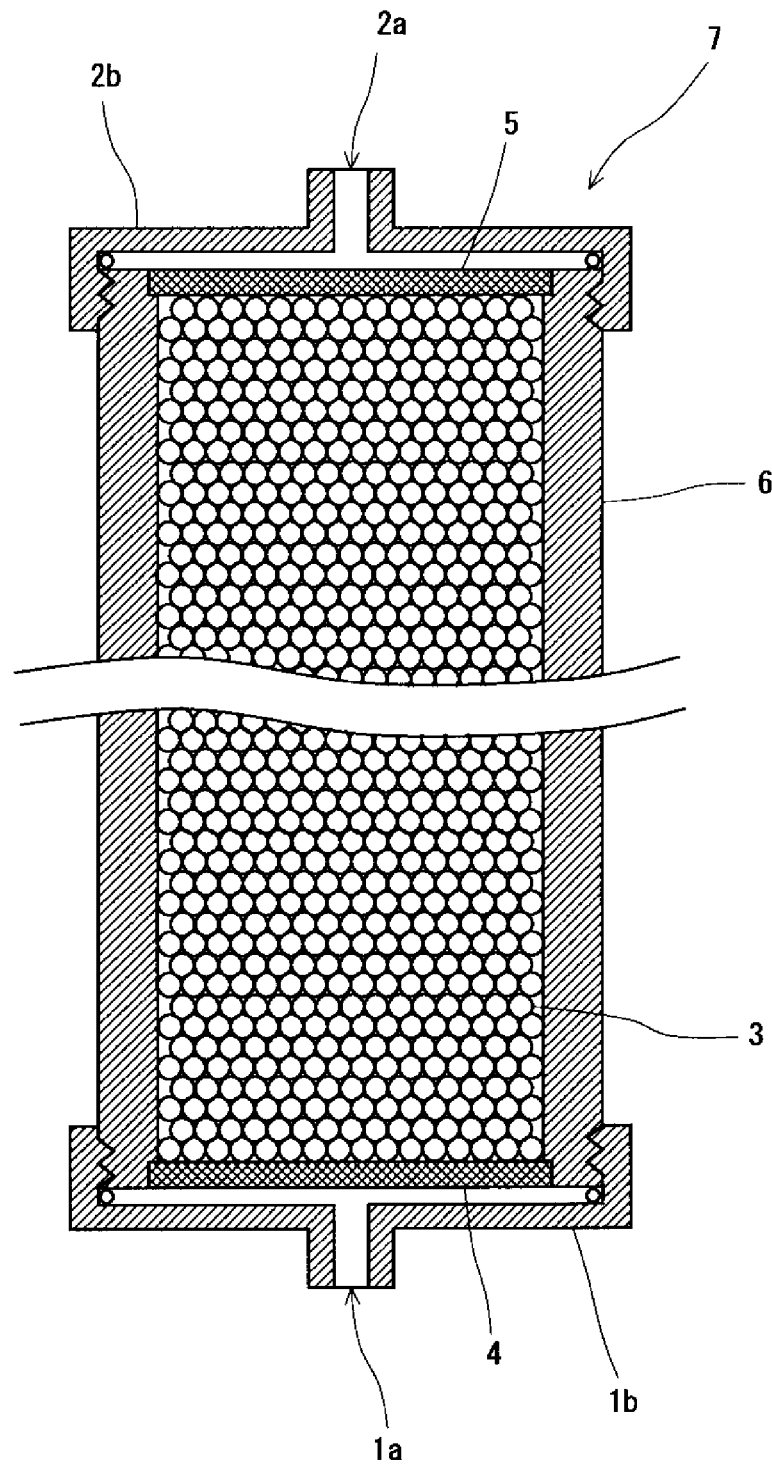

ADSORBENT FOR CALCIPROTEIN PARTICLES, ADSORPTION REMOVAL SYSTEM, AND METHOD FOR UTILIZATION THEREOF

TECHNICAL FIELD

The present invention relates to a technique of adsorbing calciprotein particles in body fluid.

BACKGROUND ART

Arterial sclerosis is caused by lifestyle-related diseases such as hypertension, diabetes, hyperlipidemia; chronic kidney disease; tobacco smoking; aging; and the like, and plaque is formed in blood vessels due to chronic inflammation of the blood vessels. The formed plaque absorbs calcium in the blood, which result in ectopic calcification. The ectopic calcification causes stenosis in arteries such as cerebral blood vessels and coronary arteries, and directly leads to diseases such as cerebral infarction, angina pectoris, and cardiac infarction. Calcium ions exist in blood vessels in the state of calciprotein particles (CPP), which is, for example, a complex of calcium phosphate and serum protein Fetuin-A, and are known for a possible causative substance for such calcification and chronic inflammation. Moreover, it has been reported that for kidney disease patients the calciprotein particles reach higher blood levels with decreasing kidney function, and the calciprotein particles cannot be removed even by dialysis treatment (Non Patent Documents 1 to 3).

To the high-risk patients with advanced arterial sclerosis, chronic kidney disease, and the like, in many cases, prevention and treatment such as administrating antiplatelet drugs to interfere with blood clotting, limiting diet to indirectly control of phosphorus blood level, and administrating phosphate binder are applied. However, some of the patients have difficulties in controlling the risks. In addition, therapeutic medication that can directly reduce calciprotein particles in the blood, and methods that can effectively remove calciprotein particles from body fluid have not been established.

RELATED ART DOCUMENTS

Non-Patent Documents

Non-Patent Document 1: Clin. Calcium. 2014 (24) 1785-92
Non-Patent Document 2: J. Am. Soc. Nephrol. 2010 (21) 1998-2007
Non-Patent Document 3: Nephrol. Dial. Transplant. 2012 (27) 1957-66

SUMMARY OF THE INVENTION

Problems to be Solved by the Invention

The present invention has been achieved by focusing on the circumstances described above, and the purpose thereof is to adsorb calciprotein particles.

Means for Solving the Problems

The present invention is as follows:
[1] An adsorbent for calciprotein particles, comprising a water insoluble carrier, wherein
a surface of the water-insoluble carrier is covalently bonded, through a hydrocarbon group, to at least one selected from the group consisting of amino groups, carboxyl groups, phosphate groups, phosphono groups, phosphino groups, and thiol groups.
[2] The adsorbent according to [1], wherein the hydrocarbon group is a linear hydrocarbon group.
[3] The adsorbent according to [1] or [2], wherein the hydrocarbon group is covalently bonded to two or more of the phosphono groups.
[4] The adsorbent according to any one of [1] to [3], wherein two of the phosphono groups and a hydroxyl group are covalently bonded to a terminal carbon atom of the hydrocarbon group, and the hydrocarbon group is a linear propyl group, a linear butyl group, or a linear hexyl group.
[5] The adsorbent according to [1] or [2], wherein one of the phosphono groups is covalently bonded to a terminal carbon atom of the hydrocarbon group, and the hydrocarbon group is an undecyl group.
[6] The adsorbent according to any one of [1] to [5], wherein the carrier is porous.
[7] The adsorbent according to any one of [1] to [6], which adsorbs calciprotein particles in body fluid.
[8] An adsorber of calciprotein particles, characterized in that the adsorber comprises a container having a liquid inlet and a liquid outlet, and the container is packed with the adsorbent according to any one of [1] to [7].
[9] A system of adsorbing calciprotein particles, characterized in that the system comprises the adsorber according to [8] and a pump for supplying liquid to the adsorber, and the system is connected to a dialyzer or a plasma separator.
[10] A process for adsorbing calciprotein particles, comprising the step of contacting the adsorbent according to any one of [1] to [7] with liquid containing calciprotein particles.
[11] A process for producing calciprotein particles removed liquid, comprising the step of contacting the adsorbent according to any one of [1] to [7] with liquid containing calciprotein particles.

Effects of the Invention

According to the present invention, calciprotein particles can be adsorbed.

BRIEF DESCRIPTION OF THE DRAWINGS

FIG. 1 is a schematic cross-sectional view showing an example of the adsorber of the present invention.

MODE FOR CARRYING OUT THE INVENTION

The purpose of the present invention is to adsorb calciprotein particles. Calciprotein particles are complexes of calcium phosphates and proteins, and more specifically, complexes of calcium phosphates (especially, Posner cluster: the component is $Ca_9(PO_4)_6$)) and Fetuin-A etc., and preferably the calciprotein particles are nanoparticles formed by polymerization of Fetuin-A etc. containing calcium phosphates. The calcium phosphates include Monetite ($CaHPO_4$), Brushite ($CaHP_4 \cdot 2H_2O$), amorphous calcium phosphate ($Ca_9PO_4)_6$), hydroxyapatite ($Ca_{10}(PO_4)_6(OH)_2$); and amorphous calcium phosphate and hydroxyapatite are preferable. The calciprotein particles may have a primary CPP structure in which calcium phosphate crystals are exposed to the surface, or a secondary CPP structure formed by phase transition of primary CPP in which calcium phosphate crystals are surrounded by Fetuin-A etc., and the primary CPP is preferable. The CPP also absorbs proteins in body fluid as complexes with calcium phosphates other than Fetuin-A, and the proteins include, for example, albumin, fibrinogen, RANKL (Receptor activator of nuclear factor kappa-B ligand), BMP-2 (Bone morphogenetic protein 2), BMP-7 (Bone morphogenetic protein 7), and Osteoprotegerin. The calciprotein particles and the proteins absorbed as complexes may be modified with groups such as a functional group for detection like fluorescent label or a reactive group that enhances bonding ability with other molecules. The modification can be made in vivo or in vitro, and may be abnormal protein formation caused by mutation of genes and the like.

The calciprotein particles can be adsorbed or removed by an adsorbent in which a water-insoluble carrier is covalently bonded to an electron-donating group through a hydrocarbon group. The electron-donating group is the part interacting with the calciprotein particles, and the hydrocarbon group is the part functioning as a spacer. Due to the spacer, the electron-donating group can be spaced from the carrier to increase the rate of contact between the electron-donating group and the calciprotein particles, which results in increased adsorbing efficiency.

The hydrocarbon group may be a linear hydrocarbon group, branched hydrocarbon group, or cyclic hydrocarbon group, all of which are preferably saturated hydrocarbon groups. The linear hydrocarbon group or the branched hydrocarbon group is more preferable, and even more preferably, linear alkyl group or branched alkyl group, and most preferably, the linear alkyl group. The number of carbon atoms of the longest part of the hydrocarbon group is, for example, 1 or more, preferably 2 or more, more preferably 3 or more, and most preferably 4 or more; and for example, 20 or less, preferably 12 or less, and more preferably 8 or less.

The electron-donating group is exemplified by a group in which a hydrogen atom is bonded to heteroatom such as N, S, and P, or a group having an acidic proton such as a group derived from oxo acid. The group in which a hydrogen atom is bonded to the heteroatom is exemplified by an amino group, thiol group, and phosphino group. The group having an acidic proton is exemplified by carboxyl group (carboxylic acid group), phosphate group, and phosphono group (phosphonic acid group). Both the group in which a hydrogen atom is bonded to the heteroatom such as N, S, P, and the group having acidic proton can be alone, or in combination of 2 or more kinds. The preferable electron-donating group is the group having an acidic proton, and more preferably, a phosphate group and a phosphono group (phosphonic acid group).

The hydrocarbon group covalently bonded to the electron-donating group is termed ligand. In the ligand, the electron-donating group can be bonded to any part of the hydrocarbon group, and it is preferable that the electron-donating group is covalently bonded to a terminal end of the hydrocarbon group. Moreover, the number of the electron-donating group covalently bonded to one hydrocarbon group is not limited to 1, and is preferably 2 or more, and particularly preferable 2 of the electron-donating groups are covalently bonded. The ligand having 2 or more of the electron-donating groups can enhance adsorbability. In the case where the ligand has 2 or more of the electron-donating groups, the number of carbon atoms between the electron-donating groups is, for example, 1 to 5, preferably 1 to 3, and more preferably 1.

In the case where the ligand has 2 or more of the electron-donating groups, at least 1 or 2 of the electron-donating groups preferably have an acidic proton. The hydrocarbon group to which 2 or more groups having an acidic proton (especially phosphono group) are bonded can easily enhance adsorbability.

To the hydrocarbon group constituting the ligand, a polar group other than the electron-donating group such as a hydroxyl group may be bonded. Working with the electron-donating group, the hydroxyl group is effective to improve the interaction with the calciprotein particles. The number of carbon atoms between the hydroxyl group and the electron-donating group is, for example, 1 to 5, preferably 1 to 3, and more preferably 1.

A preferable ligand is such that a terminal carbon atom of the hydrocarbon group (preferably linear alkyl group) is bonded to 1 or 2 of the electron-donating groups and 0 or 1 of the hydroxyl group. The most preferable ligand is exemplified by the one in which a terminal carbon atom of the linear alkyl group (especially, linear alkyl groups having about 3 to 10 carbon atoms such as linear propyl group, linear butyl group, linear hexyl group, more preferably, linear alkyl groups having 4 to 6 carbon atoms) is covalently bonded to one of the hydroxyl groups and two of the phosphono groups; and the one in which a terminal carbon atom of the linear alkyl group (especially, linear alkyl groups having about 8 to 15 carbon atoms such as linear undecyl group) is covalently bonded to one of the phosphono group.

The content of the ligand per unit volume (1 mL) of the water insoluble carrier is desirably 10 nmol or more, preferably 100 nmol or more, more preferably 1 µmol or more, and most preferably 3 µmol or more; and for example, 100 µmol or less, and preferably 50 µmol or less.

Here, the volume of the water-insoluble carrier is defined as the volume (sedimentation volume) that is determined by the following steps: precipitating the water-insoluble carrier in water while vibrating; after the completion of the precipitation, making sure that the volume of the water-insoluble carrier will not vary even if it is vibrated; determining the unvarying volume as the sedimentation volume. The amount of the water for determining the sedimentation volume is enough as long as supernatant is obtained.

The water-insoluble carrier is solid at ordinary temperatures and pressures. Various forms such as granular form, plate-like form, fibrous form, hollow fiber form, and non-woven fabric form can be adopted for the water-insoluble carrier, and its size is not particularly limited, however, it is preferable that the water-insoluble carrier has the granular form and a predetermined size range. The average grain diameter of the granular water-insoluble carrier based on the number of the grains is, for example, 10 m or more, preferably 100 µm or more, and more preferably 200 µm or more, and for example, 5 mm or less, preferably 1 mm or less, and more preferably 0.8 mm or less. The average diameter of the granular water insoluble carrier based on the number of the grains can be determined by measuring respective diameters of the carrier on an enlarged photograph under a stereomicroscope.

Being classified according to materials, the water-insoluble carrier is exemplified by inorganic carriers such as glass beads, silica gel; synthetic polymer carriers such as cross-linked polyvinyl alcohol, cross-linked polyacrylate, cross-linked polyacrylamide, and cross-linked polystyrene, and combination or copolymer thereof; organic carrier composed of polysaccharide such as crystalline cellulose, cross-linked cellulose, cross-linked agarose, and cross-linked dextrin; and composite carrier obtained in combination thereof such as organic-organic composite carrier and organic-inorganic composite carrier.

The water-insoluble carrier is preferably a hydrophile. Specifically, it is preferable that a hydrophilic group such as hydroxyl group, ether group, and amino group is exposed to the surface. Furthermore, it is preferable that the water-insoluble carrier has less non-specific adsorbability for components in body fluid, and it is also preferable that the water-insoluble carrier is superior in safety such as blood compatibility. The water-insoluble carrier having such properties is exemplified by an organic carrier composed of cross-linked polyvinyl alcohol and polysaccharide.

In addition, the water-insoluble carrier includes a carrier having porous configuration with multiple fine pores of appropriate size (a porous carrier), a carrier in which polymer network is three-dimensionally formed, and a monolithic carrier having a plurality of pores a part of which is a through hole, and is not limited thereto, however, the porous carrier is preferable.

In the case where the water-insoluble carrier is the porous carrier, the porous carrier preferably has an exclusion limit molecular weight as much as the to-be-adsorbed material (i.e. calciprotein particles) can enter into the pores. The term exclusion limit molecular weight here is the smallest molecular weight of the molecule among molecules that cannot enter into the pores when being chromatographed, which is generally described in books such as "Experimental High-Performance Liquid Chromatography, Kagakudojin" written by Hiroyuki Hatano, and Tosihiko Hanai, and generally measured with globular protein. The exclusion limit molecular weight of the porous carrier is, for example, 10,000 or more, preferably 100,000 or more, and more preferably 1,000,000 or more, and no upper limit is defined, however, too large exclusion limit molecular weight leads to reduced density of the water-insoluble carrier, which makes an adverse effect on its strength, that is to say withstanding pressure property of the water-insoluble carrier. From such a standpoint, the exclusion limit molecular weight is, for example, 100,000,000 or less, preferably 50,000,000 or less, and more preferably 10,000,000 or less.

The adsorbent can be produced for example, by bonding the hydrophilic group at the surface of the water-insoluble carrier to ligand molecules having the hydrocarbon group, the electron-donating group, and bond-forming functional group or to ligand polymers having the hydrocarbon group, the electron-donating group, and bond-forming functional group. When bonding the carrier to the ligand molecules or the ligand polymers, intermediate molecules can be used; the intermediate molecules have the first functional group reacting with the bond-forming functional group of the ligand molecules or the ligand polymers, and also have the second functional group reacting with the hydrophilic group of the water-insoluble carrier. The adsorbent is produced by bonding the bond-forming functional group of the ligand molecules or the ligand polymers to the hydrophilic group of the water-insoluble carrier or to the first functional group of the intermediate molecules.

The first functional group of the intermediate molecules is exemplified by various functional groups such as an amino group, amide group, carboxylic group (including activated carboxylic group such as carbonyl halide group, carboxylic acid anhydride group, and carboxylic acid ester group), sulfonic acid group (including activated sulfonic acid group such as sulfonyl halide group), hydroxyl group, thiol group, aldehyde group, halogen group, epoxy group, and silanol group. The second functional group of the intermediate molecules is exemplified by a halogen group, sulfonic acid group (including activated sulfonic acid group such as sulfonyl halide group), and carboxylic group (including activated carboxylic group such as carbonyl halide group and carboxylic acid anhydride group). As the intermediate molecules having both of these first functional group and second functional group are, for example, molecules having an epoxy group and halogen group (for example, epichlorohydrin etc.) are preferable. The nucleophilic substitution of the halogen group by the hydroxyl group of the water-insoluble carrier is carried out, and consequently, the intermediate molecules are bonded to the water-insoluble carrier.

The bond-forming functional group of the ligand molecules or the ligand polymers is determined according to whether the intermediate molecules are used or not. In the case where the intermediate molecules are not used, the bond-forming functional group can be a group having bonding reactivity to a hydrophilic group, and can be selected from the same range as the second functional group of the intermediate molecules. In the case where the intermediate molecules are used, as the bond-forming functional group, groups having good chemistry in combination with the first functional group of the intermediate molecules can be selected from the same range as the first functional group of the intermediate molecules.

The ligand molecules preferably have a phosphono group as the electron-donating group, a hydroxyl group that can be bonded as necessary, an amino group or thiol group as the bond-forming functional group, and a linear alkyl group as the hydrocarbon group, and particularly mercapto-n-alkyl phosphonic acid and amino-1-hydroxy-n-alkylidene bis phosphonic acid are preferable. The mercapto-n-alkyl phosphonic acid is exemplified by molecules having 1 to 20 carbon atoms such as 3-mercapto-n-propyl phosphonic acid and 11-mercapto-n-undecyl phosphonic acid, and preferably exemplified by molecules having 8 to 15 carbon atoms. The amino-1-hydroxy-n-alkylidene bis phosphonic acid is exemplified by molecules having 1 to 20 carbon atoms such as pamidronic acid, alendronic acid, and neridronic acid, and preferably exemplified by molecules having 3 to 10 carbon atoms, and more preferably molecules having 4 to 6 carbon atoms.

The adsorbent described above can process various liquid having calciprotein particles, for example, cerebrospinal fluid, blood, blood plasma, blood serum, ascites fluid, lymph fluid, joint fluid, bone marrow fluid, and various fluid elements derived from living body including fractionated components thereof. Moreover, liquid possible to include calciprotein particles such as water and buffer liquid also can be processed.

To adsorb calciprotein particles from liquid with the adsorbent, the adsorbent needs to be contacted with the liquid, and then, the adsorbent and the liquid need to be separated. For example, the adsorbent and the liquid are put in a container to contact each other by still standing or shaking, thereafter appropriate solid-liquid separation such as decant and filtration may be applied, and preferably, the adsorber comprises a container (a hollow container) having a liquid inlet and a liquid outlet and is packed with the adsorbent, which is safe and convenient. Contacting the adsorbent with the liquid can provide calciprotein particles removed liquid.

The adsorber can be exemplified by, for example, the one shown in FIG. 1. The adsorber 7 in FIG. 1 is provided with a hollow cylindrical container (a column) 6 in which granular adsorbent 3 is packed. Filter 4 and 5 are attached on both side of the hollow cylindrical container 6, which prevents the adsorbent 3 from running off while making it possible for liquid to flow through the adsorbent 3. In addition, the area of the hollow cylindrical container 6 on which the filter 4 and 5 are attached is provided with covers 1b and 2b that can be liquid-tightly fixed to the hollow cylindrical container 6 with screws etc. Through liquid inlet 1a and liquid outlet 2a formed in the cover 1b and 2b, liquid can be supplied to the adsorbent 3 in the hollow cylindrical container 6.

An adsorbing system can be constructed such that an apparatus more effective in adsorption removal of calciprotein particles is attached to the adsorber. As an example, a pump for supplying liquid can be disposed, and also a dialyzer, a plasma separator, a blood filter etc. can be connected. Furthermore, one kind or two or more different kinds of the adsorbent may be packed in the adsorber. Moreover, two or more adsorbers may be used, both of which can be packed with the same or different adsorbent. The two or more adsorbers can be connected in series or in parallel.

The adsorbing system preferably comprises the pump for supplying liquid and the adsorber. More preferably, the dialyzer or the plasma separator is connected upstream or downstream of the adsorber, which can remove calciprotein particles while dialyzing blood, separating plasma, and filtering plasma.

The present application claims priority based on Japanese Patent Application No. 2016-151390 filed on Aug. 1, 2016. All the contents described in Japanese Patent Application No. 2016-151390 filed on Aug. 1, 2016 are incorporated herein by reference.

EXAMPLES

Hereinafter, the present invention is more specifically described with reference to examples. The present invention, however, is not limited by the following examples but can also be absolutely carried out with appropriate changes to the examples within a scope in compliance with the intent described above and later, and all the changes are to be encompassed within a technical scope of the present invention.

Example 1

Alkaline aqueous solution was added to 40 mL of porous cellulose beads (the exclusion limit molecular weight: 5,000,000, the grain diameter: 400 to 500 μm) to make the total content 80 mL, and then, 30 mL of epichlorohydrin was added thereto to be reacted at 40° C. for 2 hours. After the reaction, the beads were sufficiently washed with water to obtain epoxidized cellulose beads. Pamidronic acid aqueous solution was added to the obtained epoxidized cellulose beads to be shaken at 50° C. for 5 hours or more, followed by sufficient water washing to obtain pamidronic acid immobilized cellulose beads (adsorbent A). Sulfuric acid and nitric acid were added to the adsorbent A that had been dried to be acid decomposed under pressure with a microwave decomposition unit, and the content of element P in the obtained solution was analyzed by ICP-AES method. From the elemental analysis, the immobilized amount of pamidronic acid was determined to be 2 μmol/mL.

Example 2

In the same manner as in Example 1 except changing from pamidronic acid aqueous solution to alendronic acid aqueous solution, alendronic acid immobilized cellulose beads (adsorbent B) was obtained. From the elemental analysis, the immobilized amount of alendronic acid was determined to be 5 μmol/mL.

Example 3

In the same manner as in Example 1 except changing from pamidronic acid aqueous solution to neridronic acid aqueous solution, neridronic acid immobilized cellulose beads (adsorbent C) was obtained. From the elemental analysis, the immobilized amount of neridronic acid was determined to be 6 μmol/mL.

Example 4

Ethanol aqueous solution including 11-mercapto undecyl phosphonic acid was added to the epoxidized cellulose beads obtained in Example 1 to be shaken at 40° C. for 24 hours, followed by sufficient water washing to obtain 11-mercapto undecyl phosphonic acid immobilized cellulose beads (adsorbent D). From the elemental analysis, the immobilized amount of 11-mercapto undecyl phosphonic acid was determined to be 10 μmol/mL.

Evaluation of Adsorbability 1

To 30 μL of beads of the adsorbent A, B, C, and D obtained in Examples 1 to 4, 120 μL of blood serum containing calciprotein particles (CPP) was added to be shaken at room temperatures for one hour. The amount of CPP in supernatant of the unprocessed blood serum and the blood serum after one-hour shaking is shown in Table 1.

In the above experiments, the amount of CPP was measured as follows.

Near-infrared fluorescent probe (Osteosense (registered trademark)) was added to the to-be-measured solution containing CPP to be bonded to CPP, and then, was fractionated by gel filtration spin column, after which the fluorescence derived from fractionated component of high molecular weight containing CPP was quantitated with a near-infrared scanner.

TABLE 1

| Sample | Adsorbent | The amount of calciprotein particles in supernatant after processing (fluorescence intensity) |
|---|---|---|
| Example 1 | A | 154,592 |
| Example 2 | B | 155,206 |
| Example 3 | C | 156,738 |
| Example 4 | D | 177,015 |
| Blood serum (before processing) | None | 233,032 |

INDUSTRIAL APPLICABILITY

The adsorbent of the present invention is expected to be used in prevention and treatment for various diseases that is thought to be related to accumulation of calciprotein particles in the body. In addition, liquid possible to include calciprotein particles such as body fluid can be processed with the adsorbent of the present invention to be cleaned.

DESCRIPTION OF REFERENCE SIGNS

1a: liquid inlet
2a: liquid outlet
3: adsorbent
4, 5: filter
6: hollow cylindrical container (column)
7: adsorber
1b: cover
2b: cover

The invention claimed is:

1. A process for adsorbing calciprotein particles, comprising the step of contacting an adsorbent comprising a water-insoluble carrier with liquid containing calciprotein particles,
wherein a surface of the water-insoluble carrier is covalently bonded, through a hydrocarbon group, to at least one group selected from the group consisting of an amino group, carboxyl group, phosphate group, phosphono group, phosphino group, and thiol group,
the hydrocarbon group content is 10 nmol or more per unit volume (1 mL) of the water-insoluble carrier, and
calciprotein particles are complexes of calcium phosphates and proteins.

2. The process according to claim 1, wherein the hydrocarbon group is covalently bonded to at least one selected from the group consisting of phosphate group, phosphono group, and phosphino group.

3. The process according to claim 1, wherein the water-insoluble carrier is at least one selected from the group consisting of inorganic carrier, synthetic polymer carrier, and organic carrier composed of polysaccharide.

4. The process according to claim 1, wherein the liquid containing the calciprotein particles is blood.

5. A process for producing calciprotein particles removed liquid, comprising the step of contacting an adsorbent comprising a water-insoluble carrier with liquid containing calciprotein particles,
wherein a surface of the water-insoluble carrier is covalently bonded, through a hydrocarbon group, to at least one group selected from the group consisting of an amino group, carboxyl group, phosphate group, phosphono group, phosphino group, and thiol group,
the hydrocarbon group content is 10 nmol or more per unit volume (1 mL) of the water-insoluble carrier, and
calciprotein particles are complexes of calcium phosphates and proteins.

6. The process according to claim 5, wherein the hydrocarbon group is a linear hydrocarbon group.

7. The process according to claim 5, wherein the hydrocarbon group is covalently bonded to two or more of the phosphono groups.

8. The process according to claim 5, wherein two of the phosphono groups and a hydroxyl group are covalently bonded to a terminal carbon atom of the hydrocarbon group, and the hydrocarbon group is a linear propyl group, a linear butyl group, or a linear hexyl group.

9. The process according to claim 5, wherein one of the phosphono groups is covalently bonded to a terminal carbon atom of the hydrocarbon group, and the hydrocarbon group is an undecyl group.

10. The process according to claim 5, wherein the water-insoluble carrier is porous.

11. The process according to claim 5, wherein the water-insoluble carrier is one of the group selected from granular, plate-like, fibrous, hollow fiber, and nonwoven fabric forms.

12. The process according to claim 10, wherein the water-insoluble carrier has an exclusion limit molecular weight of more than 10,000.

13. The process according claim 5, wherein the calciprotein particles in body fluid are adsorbed to the adsorbent.

14. The process according to claim 5, wherein an adsorber is used,
the adsorber comprises a container having a liquid inlet and a liquid outlet, and
the container is packed with the adsorbent.

15. The process according to claim 5, wherein the hydrocarbon group is covalently bonded to at least one selected from the group consisting of phosphate group, phosphono group, and phosphino group.

16. The process according to claim 5, wherein the water-insoluble carrier is at least one selected from the group consisting of inorganic carrier, synthetic polymer carrier, and organic carrier composed of polysaccharide.

17. The process according to claim 5, wherein the water-insoluble carrier is in granular form and an average grain diameter of the granular water-insoluble carrier based on number of grains is 10 μm to 5 mm.

18. The process according to claim 5, wherein the liquid containing the calciprotein particles is blood.

* * * * *